United States Patent [19]

Quack et al.

[11] Patent Number: 4,620,976
[45] Date of Patent: Nov. 4, 1986

[54] PEARLESCENT DISPERSION WITH GOOD FLOW PROPERTIES AND A LOW SURFACTANT CONTENT

[75] Inventors: Jochen M. Quack, Eppstein; Alwin Reng, Kelkheim; Werner Skrypzak, Liederbach; Walter Kunz, Hattersheim am Main, all of Fed. Rep. of Germany

[73] Assignee: Hoechst Aktiengesellschaft, Frankfurt, Fed. Rep. of Germany

[21] Appl. No.: 741,606

[22] Filed: Jun. 5, 1985

[30] Foreign Application Priority Data

Jun. 7, 1984 [DE] Fed. Rep. of Germany ....... 3421161

[51] Int. Cl.$^4$ .......................... A61K 7/06; A61K 7/08
[52] U.S. Cl. ...................... 424/70; 252/545; 252/546; 252/547
[58] Field of Search ........................... 424/70; 252/545

[56] References Cited

U.S. PATENT DOCUMENTS

| | | | |
|---|---|---|---|
| 4,110,263 | 8/1978 | Lindermann et al. | 424/70 |
| 4,440,744 | 4/1984 | Strasilla et al. | 424/70 |

FOREIGN PATENT DOCUMENTS

| | | | |
|---|---|---|---|
| 0133905 | 3/1985 | European Pat. Off. | 424/70 |
| 0071021 | 6/1981 | Japan | 424/70 |
| 0067510 | 4/1982 | Japan | 424/69 |
| 0067511 | 4/1982 | Japan | 424/69 |
| 2121072 | 12/1973 | United Kingdom | 424/70 |
| 2135332 | 8/1984 | United Kingdom | 424/70 |

OTHER PUBLICATIONS

Kossinki et al, 1982, vol. 96, p. 164569a.

*Primary Examiner*—Dale R. Ore
*Attorney, Agent, or Firm*—Connolly and Hutz

[57] ABSTRACT

Pearlescent dispersions consisting of a fatty acid glycol ester, a fatty acid alkanolamide, one or more surfactants of the formulae

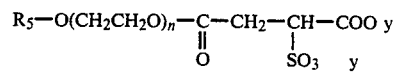

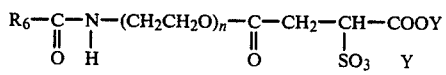

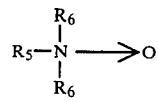

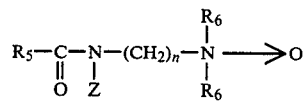

in which the individual symbols of these formulae have the meanings given in the description, salts and water in the amount to make up to 100%. Pearlescent dispersions based on these surfactants have the advantage that they already have good flow properties at temperatures below 20° C.

8 Claims, No Drawings

PEARLESCENT DISPERSION WITH GOOD FLOW PROPERTIES AND A LOW SURFACTANT CONTENT

In the preparation of cosmetic hair and body cleansing agents, washing-up agents and liquid washing and cleaning agents, substances which impart to the products mentioned a pearlescent-like appearance are frequently used to improve the optical aspect and hence to increase the commercial value. Various substances are known for achieving such a pearlescent or silky luster effect, for example pulverulent naturally occurring substances, such as mica, pearl essence, inorganic materials, such as bismuth oxychloride and titanium dioxide pigments, and furthermore metal salts of higher fatty acids, fatty glycol esters and fatty acid alkanolamides, mixed with other surfactants.

A fatty acid glycol ester, by itself or in combination with a fatty acid alkanolamide, has recently frequently been used for this purpose. These two materials are solid, non-crystalline substances. During preparation of cosmetic washing and cleansing agents with a pearlescent effect, it is necessary to warm the batch above the melting point of the substances mentioned. A homogeneous melt is thereby obtained, from which a pearlescent or silky luster effect arises, after cooling, by crystallization. However, this process has the disadvantage that the entire production batch must here be heated to a corresponding temperature (about 60°-80° C., depending on the agent which imparts pearlescence), and a more or less uniformly constant pearlescence is produced only by defined cooling and stirring conditions. This necessitates a high consumption of energy and time. Substances which are sensitive towards warming or heating, such as ethereal oils, perfume oils and particular active ingredients, can be added only after the cooling operation has ended. Likewise, there is no possibility of continuous preparation of the abovementioned cosmetic products with a pearlescent effect using this process.

Because of these disadvantages described above, processes which enable cosmetic hair and body cleansing agents with a pearlescent effect also to be prepared at room temperature have recently become established. In these processes, so-called pearlescent dispersions which are based on the most diverse agents which impart pearlescence in combination with surfactants are employed. In the preparation of these pearlescent dispersions, the substances which impart pearlescence are incorporated in a high concentration into the surfactant, which is also present in a relatively high concentration, above the melting point. Pearlescent crystals with a defined particle size distribution are thereby formed by constant, exactly matched cooling and stirring conditions. The substances which are currently most frequently used for the preparation of these pearlescent dispersions are fatty acid monoglycol and/or polyglycol esters, which are incorporated by themselves or together with fatty acid alkanolamides into aqueous solutions of alkyl sulfates or polyoxyalkylenealkyl sulfates (alkyl ether-sulfates), as solvents or dispersing agents. In most cases, very highly viscous dispersions which are no longer capable of flow at lower temperatures are formed here.

Because of the high content of alkyl sulfates or alkyl ether-sulfates, it is impossible to prepare so-called alkyl sulfate-free or alkyl ether-sulfate-free cosmetic products with these pearlescent dispersions. Because of the dioxane content in alkyl ether-sulfates, the finished products prepared with these pearlescent dispersions also have a certain content of dioxane.

Extensive studies have been carried out in order to avoid the disadvantages described for the commercially available pearlescent dispersions based on alkyl ether-sulfate. Surprisingly, it has been found that if fatty acid monoglycol and/or polyglycol esters are used in combination with fatty acid alkanolamides and particular ether-sulfate-free surfactants, as wetting or dispersing agents, pearlescent dispersions are obtained which, besides having an excellent pearlescent effect, a good storage stability and a low viscosity, do not have the abovementioned disadvantages. The surfactant content of these dispersions can be less than 2%. The pearlescent dispersion according to the invention with good flow properties consists of the following components:

5–30% by weight of a fatty acid glycol ester of the general formula I

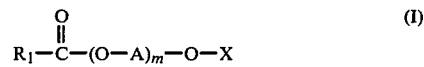

$$R_1-C(=O)-(O-A)_m-O-X \quad (I)$$

in which $R_1$ denotes a linear or branched, saturated or unsaturated hydrocarbon chain with 13–21 carbon atoms, A denotes a group of the formula $-C_2H_4-$ or $-C_3H_6-$, preferably $-C_2H_4-$, X denotes a hydrogen atom or a group of the general formula

$$R_1-C(=O)-$$

and m denotes a number from 1 to 10, preferably 1 to 3, 2–20% by weight of a fatty acid alkanolamide of the general formula II

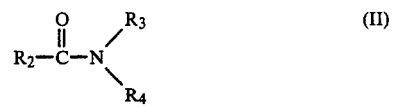

$$R_2-C(=O)-N(R_3)(R_4) \quad (II)$$

in which $R_2$ denotes a linear or branched, saturated or unsaturated hydrocarbon chain with 7–29 carbon atoms and $R_3$ and $R_4$ independently of one another denote a hydrogen atom or a group of the formula $-C_2H_4OH$ or $-C_3H_6OH$, 0.1–10% by weight of one or more surfactants of the general formulae given below

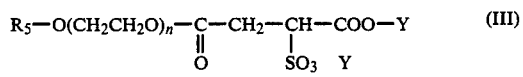

$$R_5-O(CH_2CH_2O)_n-C(=O)-CH_2-CH(SO_3Y)-COO-Y \quad (III)$$

in which $R_5$ denotes a linear or branched, saturated or unsaturated hydrocarbon group with 8–20 carbon atoms, n denotes a number from 0 to 10, preferably 2 to 5, and Y denotes an alkali metal, alkaline earth metal or ammonium ion,

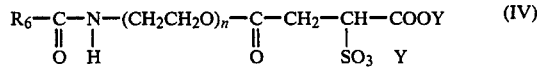

$$R_6-C(=O)-N(H)-(CH_2CH_2O)_n-C(=O)-CH_2-CH(SO_3Y)-COOY \quad (IV)$$

in which $R_6$ denotes a linear or branched, saturated or unsaturated hydrocarbon chain with 7–29 carbon atoms and n and Y have the same meaning as in formula III,

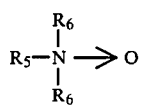

in which $R_5$ and $R_6$ have the same meaning as in the general formulae III and IV, and

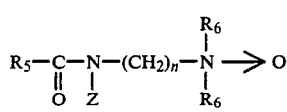

in which $R_5$, $R_6$ and n have the same meanings as in the general formulae III and IV and Z denotes a hydrogen atom or an alkyl group with 1-5 carbon atoms, 0.1 to 3%, preferably 0.5 to 1%, of a monovalent or divalent metal salt, preferably an alkali metal chloride or sulfate, and water in the amount to make up to 100%.

In the context of the abovementioned use concentrations of the individual components, observing the preparation conditions described below, optimum pearlescent dispersions are obtained which have the following advantages over the pearlescent dispersions which are currently commercially available:

(a) excellent flow properties, even at lower temperatures (below +15° C.)—this provides the possibility of continuous processing;
(b) a very low surfactant content (less than 2.0%)—this results in no charge of a certain possibly undesirable surfactant in the end formulation;
(c) freedom from alkyl ether-sulfates and
(d) a substantial reduction in the dioxane content.

To prepare the pearlescent dispersions according to the invention with optimum technological properties, the following components in the use concentrations described below are required.

Fatty acid glycol esters of the general formula I and mixtures from this class of substance are used as agents which impart pearlescence. The most favorable properties are shown by compounds in which $R_1$ is an alkyl radical with 15-17 carbon atoms, m=1 and X is a radical of the general formula $R_1$—CO—.

The use concentration of these components is preferably 10-20% by weight, the optimum concentration in the pearlescent dispersion according to the invention having been determined as 16%.

Those fatty acid alkanolamides of the general formula II which have a distribution of 8-18 carbon atoms in the starting fatty acid are preferably used. Fatty acid monoethanolamides are preferably used here, one of the two radicals $R_3$ or $R_4$ in the general formula II representing a hydrogen atom and the other radical representing a group of the formula —$C_2H_4OH$. The use concentration of these components is preferably 2-10%, in particular 4%.

Of the surfactants and surfactant mixtures mentioned of the general formulae III to VI, mixtures of the compounds of the general formulae III and V are preferably used, the alkyl chain $R_5$ denoting 10-18 carbon atoms, n preferably denoting 4 and Y denoting a sodium ion. The use concentration of these two compounds is preferably in each case 0.9% by weight. The total content of compounds of the formulae III to VI is preferably less than 2%.

The pearlescent dispersions according to the invention are prepared by the procedure as follows.

The two components A and B are taken in a vessel which can be heated, and are melted by heating at about 75° C. An aqueous solution of components C, D and E, also heated to 75° C., is added to this melt, with stirring. The stirring speed should not be too high and should be, for example, between 10 and 100 rpm. The dispersion formed is stirred at a temperature of 75° C. for about a further 30 minutes and is then cooled to a final temperature of 20°-30° C., with stirring. Cooling should be carried out at a rate according to exactly defined conditions, in particular in the same manner as is the case with the pearlescent dispersions hitherto customary, in order to achieve a constant reproducible pearlescent effect. During the cooling operation, the two components A and B start to crystallize at about 50°-60° C. and form the desired pearlescence. Besides the main components mentioned, the present pearlescent dispersion can also contain additives, such as preservatives and buffer substances, as well as salts, such as, for example, up to 3% by weight, preferably 0.5 to 1% by weight, of sodium chloride. The pH value of the dispersion is in the range from 4 to 9, and is preferably 5-8. To avoid microbial contamination, a suitable preservative is added to the present dispersion.

The present pearlescent dispersion according to the invention can be added at room temperature to liquid hair and body cleansing agents, liquid washing-up agents and liquid washing and cleaning agents. Finished products which have an excellent pearlescence are thereby obtained. The amount of the pearlescent dispersion required for this is between 1 and 10%, preferably between 2 and 5%. Since the pearlescent dispersion according to the invention has a low viscosity at temperatures above +10° C., there is the possibility of processing the dispersion with the aid of automatic pumping, metering and mixing units. This is of particular interest in the completely continuous preparation of finished products with pearlescence.

The preparation of the pearlescent dispersion according to the invention is illustrated by the following examples. The amounts are in each case based on percentages by weight. The preparation was in all cases carried out in the manner described above.

EXAMPLE 1

| Composition | |
|---|---|
| Monoethylene glycol distearate | 16.0% |
| Coconut oil acid monoethanolamide | 4.0% |
| Sodium lauryl triglycol ether-sulfosuccinate | 0.9% |
| Coconut-alkyldimethylamine oxide | 0.9% |
| Sodium sulfate | 0.6% |
| Water, preservative to | 100.0% |

EXAMPLE 2

| Composition: | |
|---|---|
| Monoethylene glycol distearate | 10.0% |
| Coconut oil acid monoethanolamide | 10.0% |
| Sodium lauryl triglycol ether-sulfosuccinate | 0.9% |
| Coconut-alkyldimethylamine oxide | 0.9% |
| Sodium chloride | 0.6% |
| Water, preservative to | 100.0% |

EXAMPLE 3

| Composition | |
| --- | --- |
| Monoethylene glycol distearate | 16.0% |
| Coconut oil acid monoethanolamide | 4.0% |
| Sodium lauryl triglycol ether-sulfosuccinate | 0.9% |
| Alkyldimethylamine oxide | 0.9% |
| Sodium chloride | 0.6% |
| Water, preservative to | 100.0% |

EXAMPLE 4

| Composition: | |
| --- | --- |
| Triethylene glycol distearate | 16.0% |
| Coconut oil acid monoethanolamide | 4.0% |
| Sodium lauryl triglycol ether-sulfosuccinate | 0.9% |
| Coconut-alkyldimethylamine oxide | 0.9% |
| Sodium chloride | 0.6% |
| Water, preservative to | 100.0% |

EXAMPLE 5

| Composition: | |
| --- | --- |
| Monoethylene glycol monostearate | 15% |
| Stearic acid monoethanolamide | 5% |
| Sodium lauryl triglycol ether-sulfosuccinate | 0.9% |
| Coconut-alkyldimethylamine oxide | 0.9% |
| Sodium sulfate | 0.6% |
| Water, preservative to | 100.0% |

EXAMPLE 6

| Composition: | |
| --- | --- |
| Triethylene glycol distearate | 16% |
| Myristic acid monoethanolamide | 4% |
| Sodium coconut-alkylamido-triethylene glycol ether-sulfosuccinate | 1% |
| Lauryl-dimethylamine oxide | 1% |
| Sodium chloride | 0.4% |
| Water, preservative to | 100.0% |

EXAMPLE 7

| Composition: | |
| --- | --- |
| Monoethylene glycol monostearate | 15% |
| Myristic acid monoethanolamide | 5% |
| Sodium lauryl triethylene glycol ether-sulfosuccinate | 0.9% |
| Coconut-alkylamidoethylenedimethylamine oxide | 1.2% |
| Sodium chloride | 0.8% |
| Water, preservative to | 100.0% |

The pearlescent dispersions according to Examples 1–4 were tested in accordance with the following criteria:
1. Evaluation of the pearlescent effect
2. Determination of the so-called "optical density"
3. Measurement of the viscosity or of the flow properties
4. Testing of the homogeneity
5. Testing of the storage stability at temperatures higher (40° C.) and lower than room temperature.

The test methods usually employed in the cosmetics industry were used. The pearlescence is evaluated visually in comparison with commercially available pearlescent dispersions. The optical density is evaluated photometrically in a dilution of 0.5 g/l of water with the aid of a turbidity measuring apparatus according to Dr. Lange. Taking into consideration these test criteria, the pearlescent dispersions described in Examples 1–4 exhibit excellent properties comparable with commercially available products. However, in contrast to these commercially available dispersions, the dispersions according to the invention already have good flow properties below 20° C.

We claim:

1. A pearlescent dispersion with good flow properties, which consists essentially of 5–30% by weight of a fatty acid glycol ester of the formula I

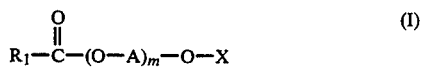

in which $R_1$ denotes a saturated or unsaturated hydrocarbon chain with 13–21 carbon atoms, A denotes a group of the formula $-C_2H_4-$ or $-C_3H_6-$, X denotes a hydrogen atom or a group of the formula

and m denotes a number from 1 to 10, 2–20% by weight of a fatty acid alkanolamide of the general formula II

in which $R_2$ denotes a saturated or unsaturated hydrocarbon chain with 7–29 carbon atoms and $R_3$ and $R_4$ independently of one another denote a hydrogen atom or a group of the formula $-C_2H_4OH$ or $-C_3H_6OH$, 0.1–10% by weight of one or more surfactants of the formulae III–VI given below

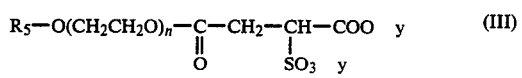

in which $R_5$ denotes a linear or branched, saturated or unsaturated hydrocarbon group with 8–20 carbon atoms, n denotes a number from 0 to 10, and Y denotes an alkali metal, alkaline earth metal or ammonium ion,

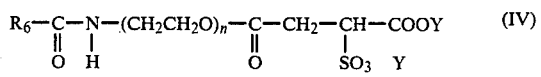

in which $R_6$ denotes a linear or branched, saturated or unsaturated hydrocarbon chain with 7–29 carbon atoms and n and Y have the same meaning as in formula III,

in which $R_5$ and $R_6$ have the same meaning as in the formulae III and IV, and

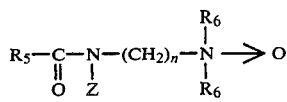

in which $R_5$, $R_6$ and n have the same meanings as in the formulae III and IV and Z denotes a hydrogen atom or an alkyl group with 1-5 carbon atoms, 0.1 to 3% of a monovalent or divalent metal salt, and water in the amount to make up to 100%.

2. A dispersion as claimed in claim 1, wherein A denotes a group of the formula —$C_2H_4$—.

3. A dispersion as claimed in claim 1, wherein m denotes a number from 1 to 3.

4. A dispersion as claimed in claim 1, wherein n denotes a number from 2 to 5.

5. A dispersion as claimed in claim 1, wherein said dispersion contains 0.5 to 1% of a monovalent or divlent metal salt.

6. A dispersion as claimed in claim 5, wherein said metal salt is an alkali metal chloride or sulfate.

7. A dispersion as claimed in 1, wherein:
A denotes —$C_2H_4$—;
m is 1 to 3;
n is 2 to 5; and
the dispersion contains 0.5 to 1% of an alkali metal chloride or sulfate as the monovalent metal salt.

8. A dispersion as claimed in claim 1, wherein the pearlescent effect has been provided by crystals of said fatty acid glycol ester of formula I and said fatty acid alkanolamide of formula II, said crystals being dispersed in an aqueous medium containing a surfactant component which is free of alkyl sulfates and alkyl ether-sulfates, said surfactant component consisting essentially of at least one surfactant of the formulae III-VI.